(12) United States Patent  (10) Patent No.: US 8,078,283 B2
Cowan et al.  (45) Date of Patent: Dec. 13, 2011

(54) SYSTEMS AND METHODS FOR IMPLANTABLE LEADLESS BONE STIMULATION

(75) Inventors: Mark W. Cowan, Fremont, CA (US); Richard E. Riley, Palo Alto, CA (US); Axel F. Brisken, Fremont, CA (US); Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 11/764,561

(22) Filed: Jun. 18, 2007

(65) Prior Publication Data

US 2007/0293912 A1 Dec. 20, 2007

Related U.S. Application Data

(60) Provisional application No. 60/805,314, filed on Jun. 20, 2006.

(51) Int. Cl.
*A61N 1/36* (2006.01)
(52) U.S. Cl. ........................................................ 607/51
(58) Field of Classification Search ...................... 607/51
See application file for complete search history.

(56) References Cited

U.S. PATENT DOCUMENTS

| | | | |
|---|---|---|---|
| 4,026,304 A | 5/1977 | Levy | |
| 4,333,469 A * | 6/1982 | Jeffcoat et al. | 607/5 |
| 4,530,360 A | 7/1985 | Duarte | |
| 4,690,144 A | 9/1987 | Rise et al. | |
| 5,309,898 A | 5/1994 | Kaufman et al. | |
| 5,405,367 A | 4/1995 | Schulman et al. | |
| 5,441,527 A | 8/1995 | Erickson et al. | |
| 5,496,256 A | 3/1996 | Bock et al. | |
| 5,547,459 A | 8/1996 | Kaufman et al. | |
| 5,556,372 A | 9/1996 | Talish et al. | |
| 5,752,924 A | 5/1998 | Kaufman et al. | |
| 6,037,704 A | 3/2000 | Welle | |
| 6,231,528 B1 | 5/2001 | Kaufman et al. | |
| 6,322,527 B1 | 11/2001 | Talish | |
| 6,366,816 B1 | 4/2002 | Marchesi | |
| 6,652,473 B2 | 11/2003 | Kaufman et al. | |
| 2004/0172083 A1 * | 9/2004 | Penner | 607/35 |
| 2006/0136004 A1 * | 6/2006 | Cowan et al. | 607/33 |

FOREIGN PATENT DOCUMENTS

DE 4330680 3/1995

OTHER PUBLICATIONS

Heckman et al., "Acceleration of tibial fracture-healing by non-invasive, low-intensity pulsed ultrasound" The Journal of Bone and Joint Surgery, vol. 76, Issue 1, pp. 26-34, 1994.

* cited by examiner

*Primary Examiner* — Eric D. Bertram
(74) *Attorney, Agent, or Firm* — Wilson Sonsini Goodrich & Rosati

(57) ABSTRACT

Systems and methods are disclosed to enhance bone growth by stimulating bone sites for bone regrowth, fusion, or grafts. The invention uses electrical stimulation of the bone site, where vibrational energy from a source is received by an implanted device and converted to electrical energy and the converted electrical energy is used by implanted electrodes to stimulate the bone site. The vibrational energy is generated by a controller-transmitter, which could be located either externally or implanted. The vibrational energy is received by a receiver-transmitter, which could be incorporated into an orthopedic device, such as pin, cage, plate or prosthetic joint used for bone healing.

10 Claims, 5 Drawing Sheets

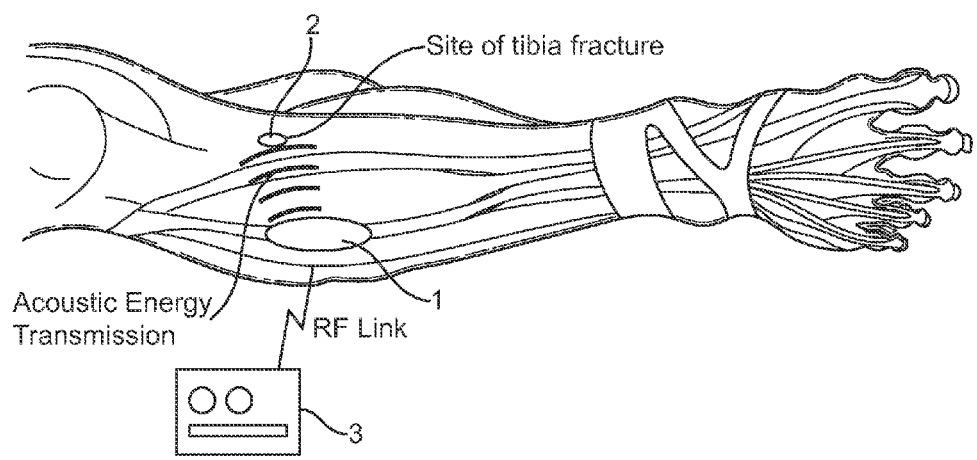
FIG. 1
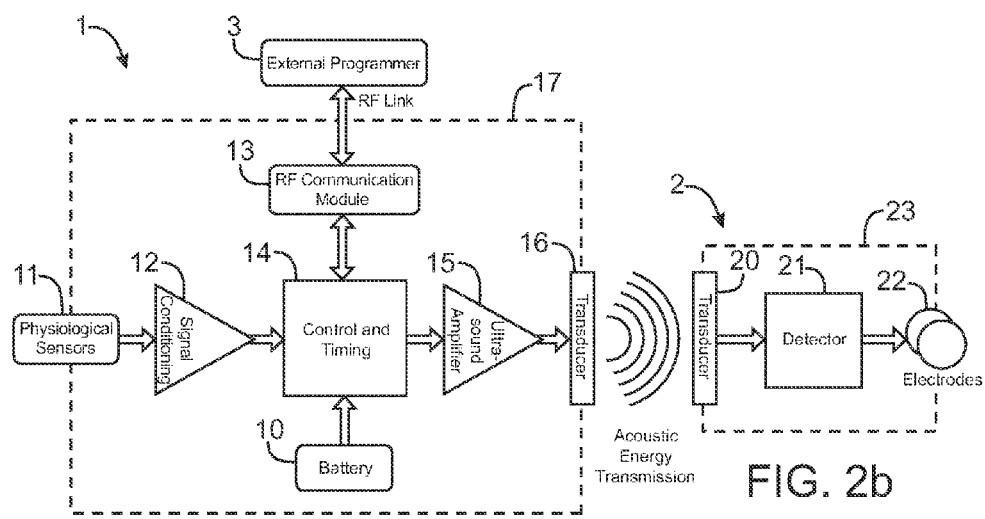
FIG. 2a
FIG. 2b

SYSTEMS AND METHODS FOR IMPLANTABLE LEADLESS BONE STIMULATION

CROSS-REFERENCES TO RELATED APPLICATIONS

The present application claims the benefit of provisional U.S. Application No. 60/805,314, filed Jun. 20, 2006, the full disclosure of which is incorporated herein by reference.

BACKGROUND OF THE INVENTION

1. Field of the Invention

The systems and methods of this invention relate to electrical stimulation treatments to enhance bone growth and fusion of bones using implantable devices. Specifically, the present invention relates to systems and methods for providing such stimulation without the use of conventional lead/electrode systems.

2. Description of the Background Art

Electrical stimulation of body tissues is used throughout medicine for treatment of both chronic and acute conditions. One such therapeutic application is using electrical stimulation to increase the rate of bone regrowth, repair, fusion of bones or bone grafts. Commonly implanted devices utilizing electrical stimulation for treatment in bone fusion are made by such companies as Biomet (Electro-Biology, Inc. (EBI)). Similarly, ultrasound energy has been used as a noninvasive therapeutic healing application in bone treatments, such as in the Exogen Bone Healing System made by Smith&Nephew.

Electrical bone growth stimulation (EBGS) generally refers to the treatment of bone fusion or repair using electrical current (direct current or alternating current). Currently, invasive use of these devices involves surgical implantation of a current generator in an intramuscular or subcutaneous space, while an electrode is implanted within the fragments of bone or bone graft at the bone fusion site. Limited by battery utilization, the implantable device typically remains functional for six to nine months after implantation; alternatively, it can be adapted to be rechargeable. Although the current generator is removed in a second surgical procedure when stimulation is completed, the electrode may or may not be removed. Noninvasive approaches that apply an electrical or electromagnetic field transcutaneously to the bone area via externally worn devices are also available. Ultrasonic bone growth stimulation (UBGS) generally refers to the treatment of bone fusion and repair using low-intensity ultrasound as an energy source and the ultrasound energy is externally applied. In noninvasive electrical applications, electrical devices require patient interaction to apply and remove electrodes. Compliance with noninvasive EBGS and UBGS is often an issue because it requires the patient to apply the therapy at a prescribed regimen and intensity. Patients may not keep batteries charged, may not comply with instructions, may fail to wear electrodes for required durations, or may adjust intensities inappropriately for the electrical bone stimulation therapy or ultrasound therapy application to be effective.

EBGS is used as an adjunct to spinal fusion surgery, with or without associated devices such as cages or screws to enhance the chances of obtaining a solid spinal fusion. EBGS has also been used as a treatment of failed spinal fusion surgery (i.e., salvage therapy). Pedicle screws and interbone cages are devices used to facilitate fusion. The role of electrical stimulation of the spine for instrumented fusions, and also in patients not considered at high risk for fusion failure, is still emerging. EBGS may be considered medically necessary as an adjunct to spinal fusion surgery for patients with risk factors for failed fusion, e.g. diabetes, renal disease, smoking, alcoholism, etc.

EBGS or UBGS is also used in appendicular skeleton for the treatment of fracture non-unions. A nonunion is considered to be established when after a period of time, since injury at the fracture site shows no visibly progressive signs of healing. Complicated variables are present in fractures, e.g., degree of soft tissue damage, alignment of the bone fragments, vascularity, and quality of the underlying bone stock. Delayed union refers to a decelerating bone healing process, as identified in serial x-rays. (In contrast, nonunion serial x-rays show no evidence of healing.) When lumped together, delayed union and nonunion are sometimes referred to as "un-united fractures."

In the appendicular skeleton, EBGS or UBGS has been used primarily to treat tibial fractures. According to orthopedic anatomy, the skeleton consists of long bones, short bones, flat bones, and irregular bones. Long bones act as levers to facilitate motion, while short bones function to dissipate concussive forces. Short bones include those composing the carpus and tarsus. Flat bones, such as the scapula or pelvis provide a broad surface area for attachment of muscles. Thus the metatarsal is considered a long bone, while the scaphoid bone of the wrist is considered a short bone. Both the metatarsals and scaphoid bones are at a relatively high risk of nonunion after a fracture.

All bones are composed of a combination of cortical and trabecular (also called cancellous) bone. Cortical bone is always located on the exterior of the bone, while the trabecular bone is found in the interior. Each bone, depending on its physiologic function, has a different proportion of cancellous to trabecular bone. However, at a cellular level, both bone types are composed of lamellar bone and cannot be distinguished microscopically.

Devices to provide EBGS may be noninvasive, with electrodes placed on the skin surface over the area of the bone to be treated. These external EBGS systems are similar to transcutaneous electrical nerve stimulators (TENS). Electrodes on the skin surface are connected to a manually adjusted stimulation controller, typically powered by batteries, which is worn by the patient on a harness or belt. In some cases it is more advantageous to implant all or part of the EBGS device. In implantable systems, the electrodes, constructed on lead wires, are placed directly on the bone, in the area of the bone, or within bone graft material. These leads are then externalized to the skin surface and connected to an external stimulation controller or more typically are arranged in a subcutaneous location where an implantable stimulation controller is subcutaneously implanted and connected to the leads. The invention described in this patent application pertains to EBGS devices in which at least one portion providing direct electrical stimulation to the bone, in the area of the bone, or within bone graft material is either permanently or temporarily implanted. The other portion, the stimulation controller, may or may not be implanted. Devices to provide UBGS are noninvasive systems: the ultrasound transmitter is placed on the skin, coupled to the body using gel, and held over the targeted bone region for the prescribed duration with a prescribed low-intensity ultrasound applied for the treatment duration.

In current practice, implanted electrical energy sources and electrode/lead wire systems are typically used to directly stimulate bone at the site of repair. Such implanted electrode/lead wires exhibit significant problems, such as infection, lead failure, and electrode/lead dislodgement. In certain applications, e.g., EBGS for treatment of bone fusions, leads are implanted at the time of bone repair surgery and left unconnected, awaiting determination of whether the bone will fuse without the aid of electrical stimulation. If the leads were externalized, then the entry/exit site in the skin must be carefully managed to avoid infection. In case of non-fusion, the leads are then connected to a stimulation controller/pulse generator. If the stimulation controller is implanted, this involves yet another procedure.

The methods and apparatus of the current invention utilize vibrational energy, particularly at ultrasonic frequencies, to overcome many of the limitations of currently known solutions for EBGS, by achieving a bone stimulation capability without the use of leads connected to a stimulation controller/pulse generator. The invention described in this patent application pertains also to UBGS devices and devices combining both UBGS and EBGS function wherein the ultrasound stimulation generator or the combined ultrasound generator and electrical stimulation controller may or may not be implanted.

The following patents, all of which are incorporated in this disclosure in their entirety, describe various aspects of using electrical stimulation for achieving various beneficial effects. U.S. Pat. No. 4,026,304 titled "Bone Generating Method and Device" by Levy describes a stimulation protocol that uses a train of pulses rather than constant direct current or voltage, using conventional lead/electrode systems. U.S. Pat. No. 5,441,527 titled "Implantable Bone Growth Stimulator and Method of Operation" by Erickson et al. describes an implantable bone growth stimulation system with electrodes implanted in the region of bone and connected via leads to an implantable stimulator/controller. U.S. Pat. No. 4,690,144 titled "Wireless Transcutaneous Electrical Tissue Stimulator" by Rise et al. describes a transcutaneous system with electrodes attached to the skin and an external controller providing for electrical field stimulation to body tissue. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation.

Additionally, the following patents describe various methods and systems for the application of ultrasonic energy for achieving beneficial effects related to bone growth or the healing of fractures using ultrasound alone: U.S. Pat. Nos. 6,231,528 and 6,652,473 both titled "Ultrasonic and Growth Factor Bone Therapy: Apparatus and Method" by Kaufman et al., U.S. Pat. Nos. 6,322,527 and 5,556,372 titled "Apparatus for Ultrasonic Bone Treatment" by Talish, U.S. Pat. Nos. 5,752,924 and 5,547,459 titled "Ultrasonic Bone Therapy Apparatus and Method" by Kaufman et al., U.S. Pat. No. 5,496,256 titled "Ultrasonic Bone Healing Device for Dental Application" by Bock et al., U.S. Pat. No. 5,309,898 titled "Ultrasonic Bone Therapy and Assessment Apparatus and Method" by Kaufman et al., and U.S. Pat. No. 4,530,360 titled "Method for Healing Bone Fractures with Ultrasound". A publication by J D Heckman, J P Ryaby, J McCabe, J J Frey and R F Kilcoyne, "Acceleration of tibial fracture-healing by non-invasive, low-intensity pulsed ultrasound" The Journal of Bone and Joint Surgery, Vol. 76, Issue 1 26-34, 1994, describes the use of a UBGS system.

BRIEF SUMMARY OF THE INVENTION

This invention relates to methods and devices for using electrical stimulation to enhance bone growth and fusion of bones and using vibrational energy as a means to transmit energy and signal information from a first device, which is implanted, to a second device containing means to receive such vibrational energy and converting it into electrical energy and then applying that electrical energy to stimulating electrodes. The second device is intended to be either permanently or temporarily implanted with stimulating electrodes in direct contact or in close proximity with the bone or bone graft material to be stimulated. In another embodiment, the first device is not implanted, but located externally.

This application of leadless electrical stimulation is for accelerating bone healing by stimulation. Bone healing includes bone fractures, bone fusions, or joint replacement that may also involve the surgical attachment of associated devices, e.g., pins, cages, plates, or bone grafts. The invention is a system comprising a controller-transmitter, an implanted receiver-stimulator, and stimulation electrodes, such that the stimulation electrodes would be in contact with bone, in close proximity to the bone, or in contact or proximity to devices used to facilitate the bone fusion/repair. In other embodiments, the receiver-stimulator would be directly incorporated into the associated device, e.g., pin, cage, plate, graft material/process, or prosthetic joint with electrodes placed as appropriate to stimulate the bone in a desired location or locations.

In one embodiment, the controller-transmitter could be implanted. In another embodiment, the controller-transmitter could be located on the external surface of the body. The transmitted vibrational energy would be directed to the receiver-stimulator to cause electrical stimulation at the electrodes of the receiver-stimulator to enhance bone healing. When located externally, the controller-transmitter could be attached to a strap, belt, or harness, or incorporated into or beneath a cast. Transmission of vibrational energy and application of electrical stimulation could be applied continuously, or temporarily at prescribed intervals when periodic stimulation is sufficient. After the fracture or fusion has healed the internal receiver-stimulator may stay at the implant site or be removed.

In another embodiment, the system is adapted to simultaneously provide ultrasonic bone treatment with electrical stimulation. In such a system, the vibrational energy from the controller-transmitter is delivered at ultrasonic frequencies with other characteristics such as are known to enhance bone growth and promote healing. Such a controller-transmitter is either implanted or externally applied. The implanted receiver-stimulator, as previously described, is adapted to intercept at least a portion of the applied ultrasonic energy and convert it to electrical energy for direct electrical stimulation of the desired site. Such a combination of ultrasonic and electrical bone growth stimulation provides enhanced therapy relative to either technique alone.

BRIEF DESCRIPTION OF THE DRAWINGS

FIG. 1 is a schematic showing the leadless bone stimulation system in application at a tibial fracture site.

FIGS. 2a and 2b are block diagrams showing the components of the acoustic controller-transmitter and acoustic receiver-stimulators of the present invention.

DETAILED DESCRIPTION OF THE INVENTION

The systems and devices described here comprise a controller-transmitter device that will deliver vibrational energy and information to one or more implanted receiver-stimulator device(s) that will convert the vibrational energy to electrical energy of a form that can be used to electrically stimulate bone. The vibrational energy can be applied with ultrasound as a single burst or as multiple bursts or as a continuous wave with appropriate selection of the following parameters:

| Parameter | Value Range |
|---|---|
| Ultrasound frequency | 20 kHz-10 MHz |
| Burst Length (#cycles) | 3-continuous |
| Stimulation Pulse Duration | 0.1 µsec-continuous |
| Duty Cycle | 0-100% |
| Mechanical Index | <1.9 |

The controller-transmitter device contains one or more ultrasound transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants can function simultaneously. It is also possible for multiple devices to function independently, either by responding only to a specific transmitted frequency, or through the use of a selective modulation technique such as pulse width modulation, or through encoding techniques such as time-division multiplexing. Further, the characteristics of the acoustic energy generated by the controller-transmitter, including the frequency, burst length, duty cycle, and mechanical index are selected such that stimulation of bone growth occurs due to the insonification of the bone tissue, as is previously known in the art. Such ultrasonic stimulation would be simultaneously present with the applied electrical stimulation of this invention to provide a combined therapy more beneficial than either ultrasonic or electrical stimulation alone. In this adaptation, the receiver-stimulator device would be constructed to operate at the same acoustic parameters required for ultrasonic stimulation and would intercept at least a portion of the applied acoustic energy for conversion into electrical stimulation energy.

In the implanted version, the controller-transmitter device containing the transmitting transducer is implanted typically just beneath the skin in the subcutaneous space. In the non-implanted version, the transducer portion is placed over the skin near the targeted bone and acoustic gel or other means is placed between the transducer face and the skin surface to ensure adequate acoustic coupling.

Figure 3:
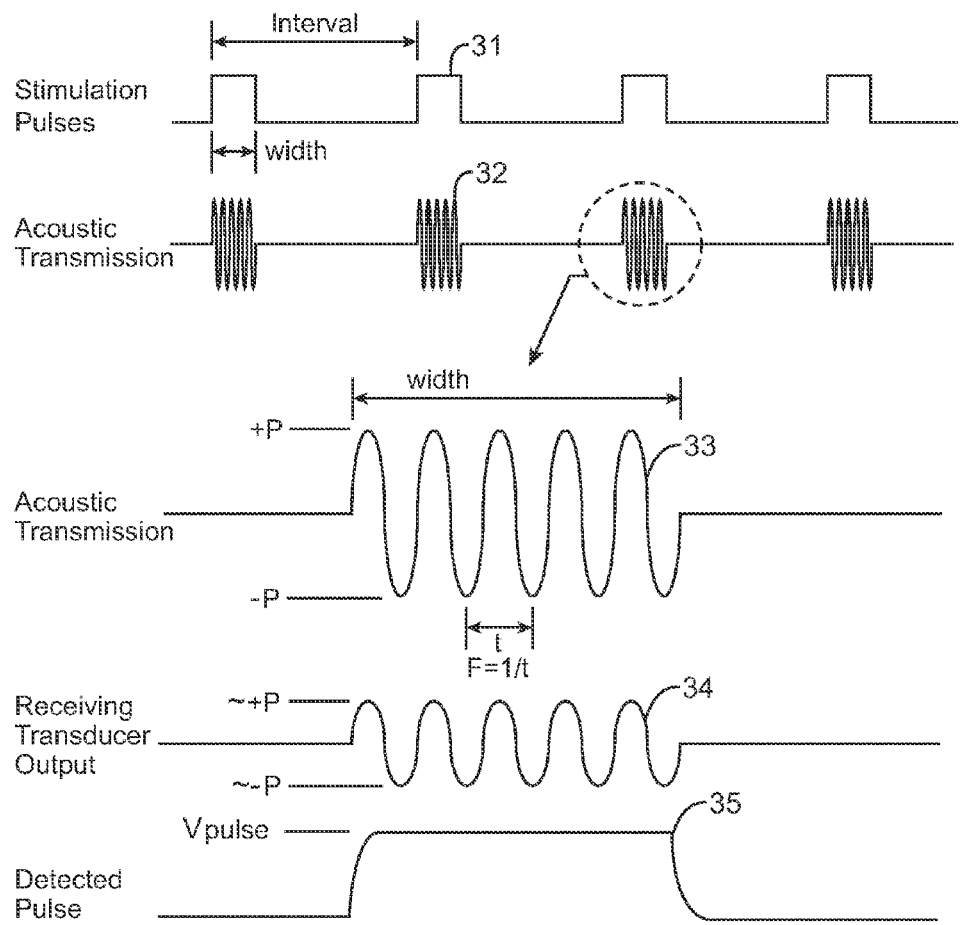
FIG. 3 illustrates representative acoustic and electrical signals useful in the systems and methods of the present invention.

An example of such an electro-acoustic stimulation system as a simple bone stimulation system is illustrated in FIGS. 1, 2, and 3.

In FIG. 1, a controller-transmitter device 1 containing circuitry to provide stimulation control and ultrasound transmission, plus means to communicate with an outside programmer 3 is implanted just beneath the skin, and generally oriented such that the transmission is over the targeted bone fracture site. An ultrasound signal is transmitted by this device 1 through intervening tissue to the receiver-stimulator device 2 containing means to receive this acoustic energy and convert it into an electrical current which may then be applied to the attached electrodes. Alternatively, the ultrasound transmission is configured such that the targeted bone fracture site receives sufficient ultrasonic energy to promote bone healing, in addition to providing the receiver-stimulator device with sufficient energy to provide electrical stimulation. In FIG. 1, this receiver-stimulator device 2 is shown attached to a section of bone in a tibial fracture. However, it should be noted that the receiver-stimulator 2 could also be attached to any bone or site near any bone that is the target of treatment. The receiver-stimulator device 2 is shown here as a small button-shaped device that would be affixed to the bone. Other appropriate shapes could be cylindrical, hexagonal, oblong, etc. Alternatively, the functional components of the receiver-stimulator may also be separated. In one embodiment (not shown) the electrodes are applied directly to the bone or to tissue near the bone and connected by small wires to the receiver. This embodiment would adapt the electrode to be shapeable, malleable configurations that conform to the bone as flexible wraps, cages, bindings, etc. or that could be placed near the bone. Electrodes may be adapted that are round, long, segmented, etc. to increase surface area or to control current density at the electrode. Electrodes may be placed on opposing sides of the bone in linear alignment with the bone or in any arrangement suitable for the size and location of the bone and the targeted bone healing site.

FIGS. 2a and 2b show more details of the system described above and shown in FIG. 1. In FIG. 2a the controller-transmitter device 1 comprises: a battery 10, one or more sensors 11, signal processing circuitry 12, a communications module 13, a control and timing module 14, an ultrasound amplifier 15, an ultrasound transducer 16. The battery 10 which provides power for the controller-transmitter may be of a type commonly used in implanted medical devices such as a lithium iodine cell or lithium silver vanadium oxide cell made by Greatbatch, Inc. or which is optionally a rechargeable battery. The one or more sensors 11 are used to detect physiological parameters, such as impedance, temperature, motion, strain, pressure, etc. Sensors may be chosen to measure acute response or to measure chronic progression of response. Suitable sensors are known for the detection of impedance, temperature, motion, strain, pressure, and the like. These sensors are connected to signal processing circuitry 12 and used by the circuitry to adjust delivery of stimulation therapy or to communicate diagnostic information from the sensors. The communications module 13 provides a data path to allow the physician to set device parameters and to acquire diagnostic information about the patient and/or the device. The data path may be by an RF communication link, magnetic coupling, ultrasound pulses, or the like, and would communicate to and from an external unit 3. Device parameters would be used by the control and timing module 14. Device parameters would include adjustments to transmissions, such as power amplitude, pulse duration, duty cycle, and the like. The control and timing module 14 uses device parameters in conjunction with the acquired physiological data to generate the required control signals for the ultrasound amplifier 15 which in turn applies electrical energy to the ultrasound transducer 16 which in turn produces the desired acoustic beam. The controller-transmitter device 1 is encased in a hermetically sealed case 17 constructed of a biologically compatible material, typical of currently existing EBGS devices.

Referring to FIG. 2b, the receiver-stimulator device 2, implanted in the path of the acoustic beam at the location where electrical stimulation is desired, contains an ultrasound transducer 20, an electrical circuit 21, and electrodes 22. Ultrasound transducer 20, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 21 which may be one of a type commonly known as an envelope detector, and which may have one of many known circuit configurations, for example a full-wave rectifier, a half-wave rectifier, a voltage doubler or the like. Electrical circuit 21 produces a voltage pulse with amplitude proportional to the amplitude of the transmitted ultrasound burst and with a pulse length generally equal to the length of the transmitted burst. The circuit 21 may also be of different configurations and functions, and provide output signals having characteristics other than a pulse. This signal is applied then to electrodes 22 made typically of platinum, platinum-iridium, gold, or the like which may be incorporated onto the outer surface of the device, and thus in direct contact with the bone or within close proximity of the bone which is to be treated by stimulation. Alternatively, the electrodes 22 are connected via wires to a main body that consists of the transducer 20 and electrical circuit 21 and the electrodes 22 are adapted to be shapeable, malleable configurations that conform to the bone as flexible wraps, cages, bindings, etc. or that could be placed near the bone. Electrodes may be adapted that are round, long, segmented, etc. to increase surface area or to control current density at the electrode. Electrodes may be placed on opposing sides of the bone or in linear alignment with the bone or in any arrangement suitable for the size and location of the bone and the targeted bone healing site. The receiver-stimulator device 2 is also enclosed within a sealed case 23 of biologically compatible material Referring also to previously described FIGS. 2a and 2b, FIG. 3 provides detail representing example acoustic and electrical signals of the present system. FIG. 3 first depicts a train of electrical stimulation pulses 31 which have a desired width and are repeated at a desired interval. The controller-transmitter device 1 produces acoustic transmissions 32, for the desired stimulation pulse width and repeated at the desired stimulation pulse interval, which are emitted from the ultrasound transducer 16. Below the waveform 32 is shown an enlargement 33 of a single acoustic burst. This burst again has a desired width, a desired oscillation frequency $F=1/t$, and also a desired acoustic pressure indicated by the peak positive pressure P+ and peak negative pressure P−. The acoustic pressure wave, when striking the receiving transducer 20 of the receiver-stimulator device 2 generates an electrical signal 34 having frequency and burst length matching that of the transmitted waveform 33 and amplitude proportional to the transmitted acoustic pressure (∼+/−P). This electrical waveform is then rectified and filtered by the circuit 21 producing the desired pulse 35 with length equal to the burst length of the transmitted waveform 33 and amplitude ($V_{PULSE}$) proportional to the amplitude of the electrical signal 34. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 21 could be configured to produce a direct current (DC) output or an alternating current (AC) output, or an output with any arbitrary, predetermined waveform. Varying the use of signal information within the ultrasound transmission for pulse duration, pulse amplitude, and duty cycle would result in any type of burst sequencing or continuous delivery waveform effective for bone growth and healing. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening tissue, spatial location of the receiver-stimulator device with respect to the transmitted ultrasound beam, as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to adjust automatically using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 4:
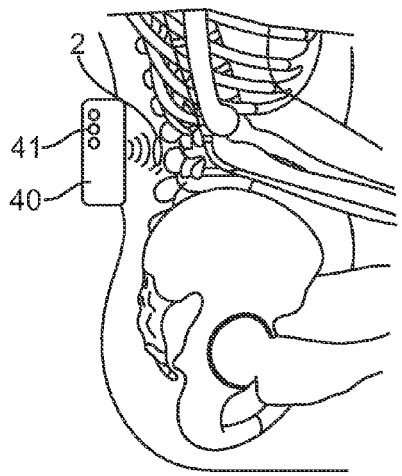
FIG. 4 is a schematic showing the leadless bone stimulation system in application at the spine.

Another embodiment of the system is illustrated in FIG. 4. In an application of an electro-acoustic stimulation system for the treatment of spinal fusion, a receiver-stimulator device 2 is shown implanted near the spinal column, with electrodes placed so as to provide electrical stimulation to a specific region of the spine. An external acoustic controller-transmitter device 40 is placed over the area of the implant to activate the stimulation. The external transmitter 40 may be handheld, or worn on the body, attached by a belt, harness, or the like. Controls 41 may be provided to allow the user to adjust ultrasound parameters. Such ultrasound parameters, possibly including amplitude, pulse duration, and pulse repetition frequency, are selected to effect fusion of the bone or bone graft. The external controller-transmitter 40 would comprise an adjustable pulse/frequency generator, ultrasound amplifier, ultrasound transmitter, and battery. Optionally, the battery may be a rechargeable type.

In another embodiment of this invention, the controller-transmitter unit shown in FIG. 4 could be implanted to enable long-term continuous treatment to the spine.

Figure 5A:
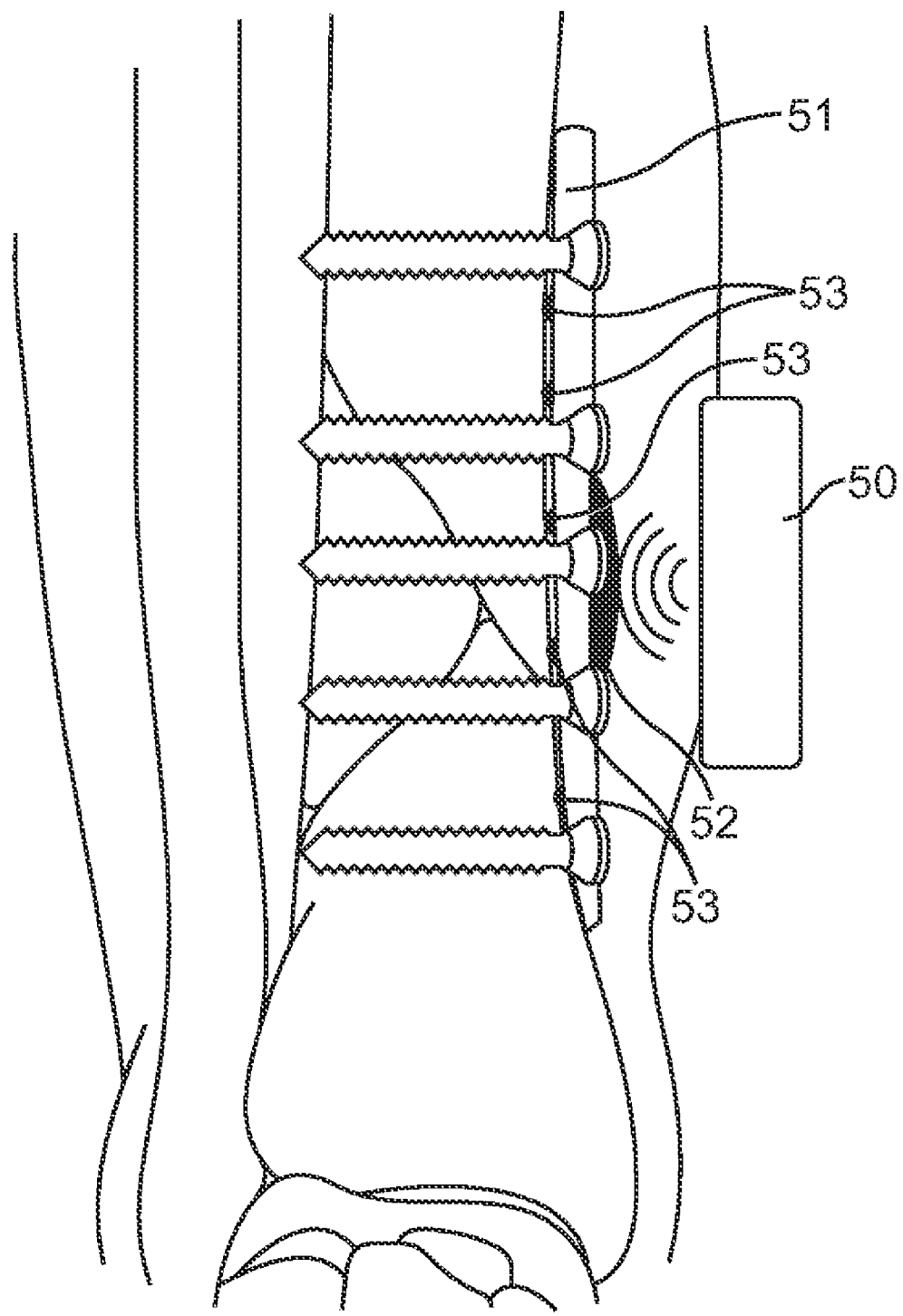
FIGS. 5a, 5b, and 5c are schematic illustrations showing components of the present invention adapted for use with devices commonly used for connecting bone fractures.
Figure 5B:
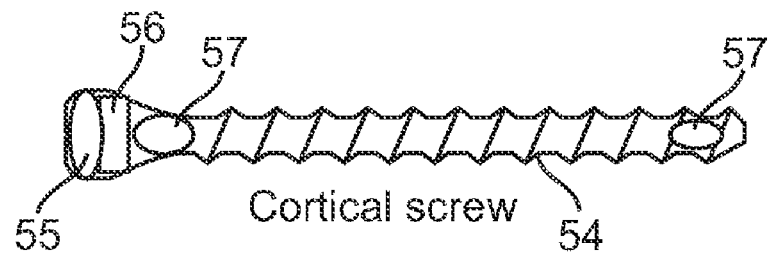
Figure 5C:
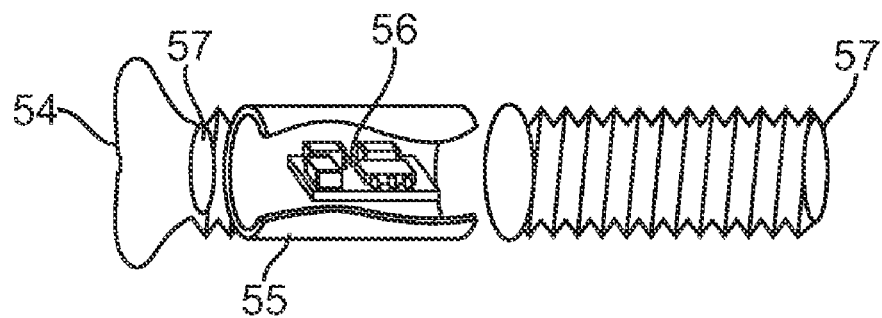

In a different embodiment of this invention, the implanted receiver and stimulation components are incorporated into an associated implanted device. For example, the receiver and stimulation components can be part of a pin, a rod, a cage, or plate used to stabilize a fracture. In such a combined device, the receiver-stimulator is adapted into the form of the associated device to provide the electrical stimulation to facilitate fusion. Referring to FIG. 5a, a metal plate 51 is attached with screws in a typical application to stabilize a severely fractured tibia. In this case the receiving transducer and detector electronics 52 and multiple electrodes 53 are incorporated onto the metal plate, with the electrodes in contact with the bone. An external controller-transmitter device 50 similar to that described above is placed over the implanted plate and held in place with a strap or harness and energized as prescribed. Alternatively the controller-transmitter can be of the type that is fully implanted. Additional applications of such a system are, for example, the incorporation of the receiver-stimulator device into the structure of a prosthetic joint or patched in place while applying bone graft materials. Referring to FIGS. 5b and 5c, a cortical screw 54 is adapted to be a receiver-stimulator including the receiving ultrasound transducer 55, circuitry 56 and electrodes 57. Similarly other associated devices for bone fusion may be adapted to contain the receiving, circuitry, and electrode elements and be used as the receiver-stimulator in the system.

Though the uses and configurations differ among the above described example bone stimulation devices, all share the same basic components of a transmitting device and one or more implanted receiver-stimulator devices. The transmitting device, whether in implantable or externally-applied embodiments, and the typical functions that may be incorporated into the transmitting device, have been described. The receiver-stimulator device, in particular with respect to the receiving ultrasound transducer, will have characteristics that are optimized for certain applications.

Figure 6A:
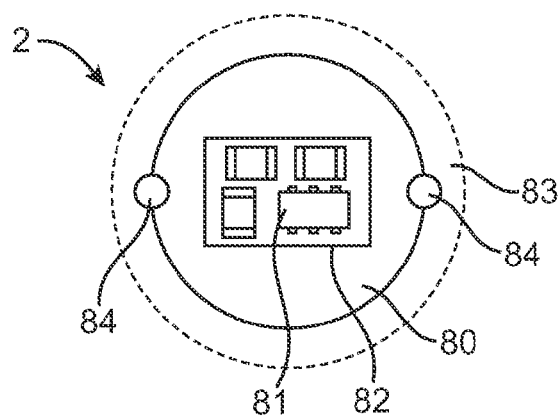
FIGS. 6a through 6c depict various embodiments for an implantable receiver-stimulator utilizing a planar transducer.
Figure 6B:
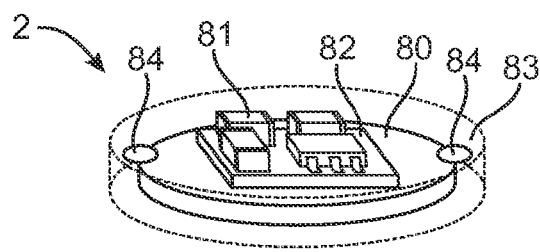
Figure 6C:
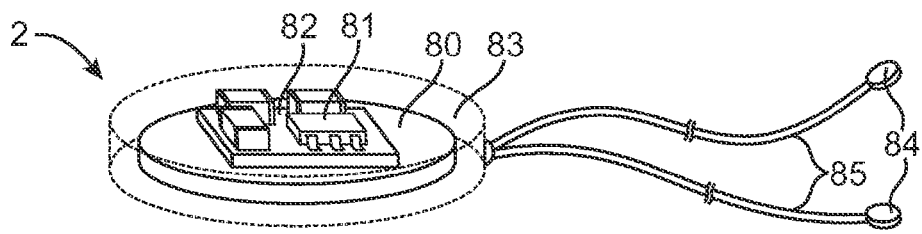

FIGS. 6a through 6c depict various possibilities for an implantable receiver-stimulator using a planar transducer. Such an embodiment may, for example, be suitable for surgical implantation for stimulation of bone or may be suitable for incorporation into associated devices such as orthopedic plates or prostheses. FIGS. 6a and 6b show in plan and perspective views, respectively, a receiver-stimulator device 2 having a circular planar ultrasound transducer 80, made typically of a piezoelectric ceramic or single crystal material having electrical contacts deposited on the top and bottom planar surfaces. The size of the ultrasound transducer 80 is selected, for example to be less than one-half wavelength, to optimize receiver sensitivity with respect to orientation. On one surface of the transducer is mounted a circuit assembly 82 containing circuit components 81, the transducer being electrically connected to the circuit components by wiring (not shown). To control any acoustic effects due to combining the components in the receiver-stimulator, the design for mounting of the circuit assembly 82 with the transducer is appropriately chosen; for example, use of air gaps or equivalent. The output of the circuit is connected to two or more stimulation electrodes 84 which are mounted on the outside of an acoustically transmissive and biocompatible casing 83 which also hermetically seals the transducer and circuitry. Electrodes 84 may be positioned on any surface or surfaces of case 83. The planar transducer 80 and case 83 may be circular as shown, or any other shape that may be suitable to the application or intended implant location.

In FIG. 6c, a receiver-stimulator 2 similar to that of FIGS. 6a through 6b is shown, though electrodes 84 are now shown disposed remotely from the case 83, located at the ends of flexible cables 85. Such an embodiment would facilitate precise placement of the stimulating electrodes, perhaps in a situation where it would be otherwise inconvenient or impossible to locate a device having integrated electrodes, as on opposing sides of a bone fracture.

An additional potential benefit of the bone-healing stimulator lies in the reported beneficial aspects of ultrasound exposure alone in accelerating the healing of both bone and soft tissue (bone/ligament/tendon) injuries. In all these devices, combined electrical and ultrasound stimulation would be delivered, providing an enhanced treatment compared to either electrical or ultrasound stimulation alone.

In another embodiment of this invention, the implanted bone stimulation electrodes could be used to deliver therapeutic agents. It is well established that an electric field or ultrasonic field could be beneficially used to enhance the transport of molecules through biological tissue (e.g., iontophoresis, electroporation, or sonophoresis). In one embodiment of this invention, the stimulating electrodes could be coated with a sustained release formulation of a beneficial agent. In another embodiment a reservoir containing a beneficial agent could be attached to the stimulating electrodes. Each time the electrodes are activated the beneficial agent could be released. In yet another embodiment the acoustic energy itself acts as a trigger to release beneficial agent that is contained in a reservoir or in a membrane or the like that is a component of the receiver-stimulator. The beneficial agent could be a bone growth factor, bone cement, stem cells that promote bone healing and growth and the like.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:
1. A method for bone stimulation therapy comprising:
implanting a bone attachment device at a bone healing site, wherein a receiver-stimulator is housed within the bone attachment device;
generating acoustic energy using a controller-transmitter, wherein the controller-transmitter comprises one or more sensors;
receiving the acoustic energy by means of the receiver stimulator;
converting the received acoustic energy into electrical bone stimulation energy using the receiver stimulator based on energy and signal information included in the generated acoustic energy;
wherein the bone attachment device comprises one or more stimulation electrodes connected to the receiver stimulator, such that the stimulation electrodes lie in electrical communication with the bone healing site, and the bone healing site is chosen to treat for bone regrowth, bone repair, fusion of bones, or fusion of bone grafts;
delivering the electrical bone stimulation energy to the bone healing site using the one or more stimulation electrodes;
sensing the electrical bone stimulation energy, wherein the sensors are adapted to sense the electrical bone stimulation energy; and adjusting the acoustic energy generated by the controller-transmitter to compensate for changes in the electrical bone stimulation energy.

2. A method of claim 1 wherein the controller transmitter is externally located.

3. A method of claim 1, wherein the sensors are configured to detect one or more physiological parameters.

4. A method of claim 1, wherein the controller-transmitter comprises a hermetically sealed housing and wherein the one or more sensors are disposed at least partly within the housing.

5. A method of claim 4, wherein the one or more sensors have a portion within the housing and a portion external to the housing.

6. A method of claim 4 or 5, wherein the one or more sensors are directly connected to a signal processing circuitry of the controller-transmitter.

7. A method of claim 1, further comprising: using an external programmer to program one or more settings of the controller-transmitter.

8. A method of claim 7, wherein the external programmer transmits a radiofrequency signal and the controller-transmitter comprises circuitry for receiving the radiofrequency signal.

9. A method of claim 1, wherein the receiver-stimulator consists essentially of an ultrasound transducer which generates a stimulation signal in response to the acoustic energy transmitted by the controller-transmitter, circuitry which rectifies the stimulation signal, and wherein the one or more stimulation electrodes deliver the rectified signal to bone tissue.

10. A method of claim 1, wherein the bone attachment device is a screw, rod, pin, cage, plate, prosthetic joint, or bone graft.

* * * * *